United States Patent
Takeuchi et al.

(10) Patent No.: US 10,391,039 B2
(45) Date of Patent: Aug. 27, 2019

(54) AL$_2$O$_3$-FREE LITHIUM SILICATE GLASS COMPOSITION

(71) Applicant: SHOFU INC., Kyoto (JP)

(72) Inventors: Daisuke Takeuchi, Kyoto (JP); Mitsuji Teramae, Kyoto (JP)

(73) Assignee: SHOFU INC., Kyoto (JP)

( * ) Notice: Subject to any disclaimer, the term of this patent is extended or adjusted under 35 U.S.C. 154(b) by 0 days.

(21) Appl. No.: 15/475,494

(22) Filed: Mar. 31, 2017

(65) Prior Publication Data

US 2017/0281473 A1    Oct. 5, 2017

(30) Foreign Application Priority Data

Mar. 31, 2016  (JP) ................. 2016-073117

(51) Int. Cl.
| | |
|---|---|
| C03C 3/097 | (2006.01) |
| C03C 3/076 | (2006.01) |
| C03C 10/04 | (2006.01) |
| A61K 6/027 | (2006.01) |
| A61K 6/02 | (2006.01) |
| A61C 5/77 | (2017.01) |
| C03B 32/02 | (2006.01) |
| C03C 4/00 | (2006.01) |
| A61K 6/00 | (2006.01) |

(52) U.S. Cl.
CPC .............. *A61K 6/0205* (2013.01); *A61C 5/77* (2017.02); *A61K 6/0005* (2013.01); *A61K 6/0082* (2013.01); *A61K 6/024* (2013.01); *A61K 6/0273* (2013.01); *C03B 32/02* (2013.01); *C03C 3/097* (2013.01); *C03C 4/0021* (2013.01)

(58) Field of Classification Search
CPC ......... C03C 10/00; C03C 3/097; C03C 3/083; A61K 6/0273
See application file for complete search history.

(56) References Cited

U.S. PATENT DOCUMENTS

| | | | | |
|---|---|---|---|---|
| 3,816,704 A | * | 6/1974 | Borom | C03C 3/097 219/455.12 |
| 5,968,856 A | * | 10/1999 | Schweiger | C03C 10/0009 106/35 |
| 6,342,458 B1 | * | 1/2002 | Schweiger | C03C 10/0009 106/35 |
| 6,420,288 B2 | * | 7/2002 | Schweiger | C03C 4/0021 106/35 |
| 6,514,893 B1 | * | 2/2003 | Schweiger | C03C 10/0009 501/5 |
| 6,606,884 B2 | * | 8/2003 | Schweiger | C03C 10/0009 65/17.6 |
| 8,546,280 B2 | | 10/2013 | Apel et al. | |
| 9,701,575 B2 | * | 7/2017 | Harryson | A61K 6/0273 |
| 2002/0010063 A1 | * | 1/2002 | Schweiger | C03C 4/0021 501/5 |
| 2003/0083188 A1 | * | 5/2003 | Seto | C03C 3/087 501/71 |
| 2006/0084562 A1 | * | 4/2006 | Oyama | C03C 3/091 501/66 |
| 2011/0030423 A1 | | 2/2011 | Johannes et al. | |
| 2015/0140274 A1 | | 5/2015 | Burke et al. | |
| 2017/0290641 A1 | * | 10/2017 | Kim | A61C 5/77 |

FOREIGN PATENT DOCUMENTS

| | | | |
|---|---|---|---|
| CA | 2252660 | 5/1999 | |
| CA | 2 851 577 | 4/2013 | |
| DE | 197 50 794 | 6/1999 | |
| EP | 0827941 A1 | * 3/1998 | ........... C03C 4/0021 |
| EP | 2 765 979 | 4/2013 | |
| JP | 5156031 | 12/2012 | |
| WO | 2012/091201 | 7/2012 | |

OTHER PUBLICATIONS

Extended European Search Report dated Aug. 31, 2017 in European Application No. 17164068.3.

* cited by examiner

*Primary Examiner* — Karl E Group
(74) *Attorney, Agent, or Firm* — Wenderoth, Lind & Ponack, L.L.P.

(57) ABSTRACT

To provide a dental lithium silicate glass composition capable of providing a dental lithium silicate glass ceramic capable of efficiently precipitating the main crystals (lithium disilicate and/or lithium metasilicate) even after heat treatment.
To provide a Al$_2$O$_3$-free dental lithium silicate glass composition including the following components: SiO$_2$: 60.0 to 80.0% by weight, Li$_2$O: 10.0 to 17.0% by weight, K$_2$O: 0.5 to 10.0% by weight, ZrO$_2$: 0.0 to 5.0% by weight, a nucleating agent: 1.0 to 6.0% by weight, a glass stabilizer: 0.0 to 8.0% by weight and a colorant: 0.0 to 10.0% by weight.

17 Claims, 4 Drawing Sheets

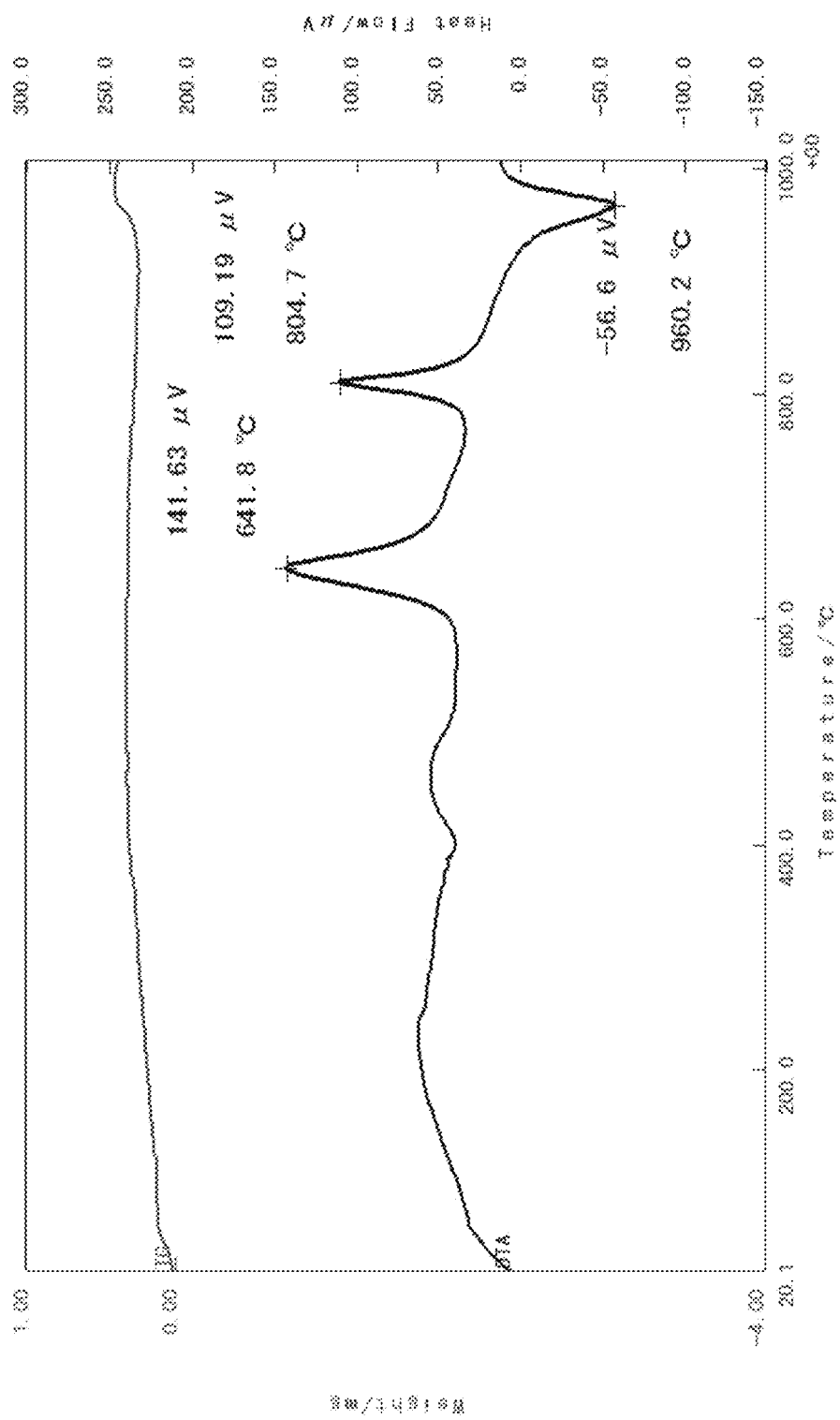
[FIG. 1]

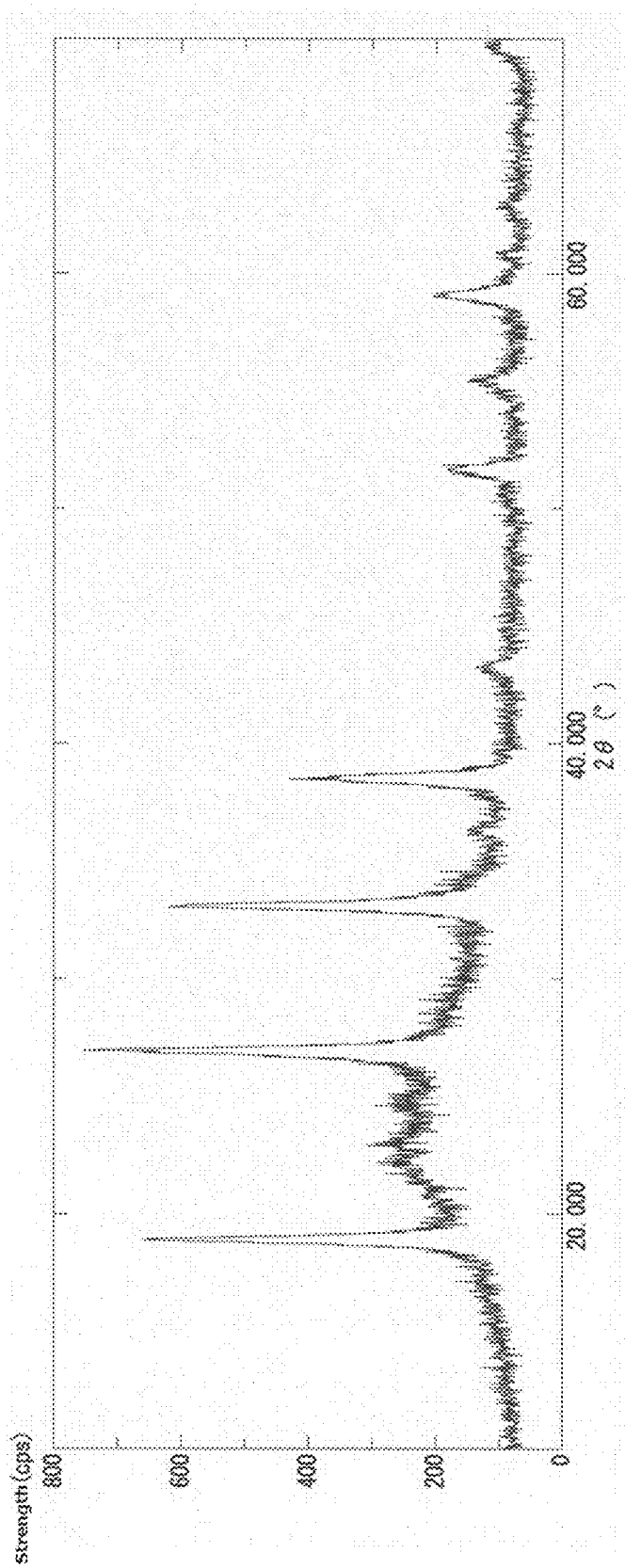
[FIG. 2]

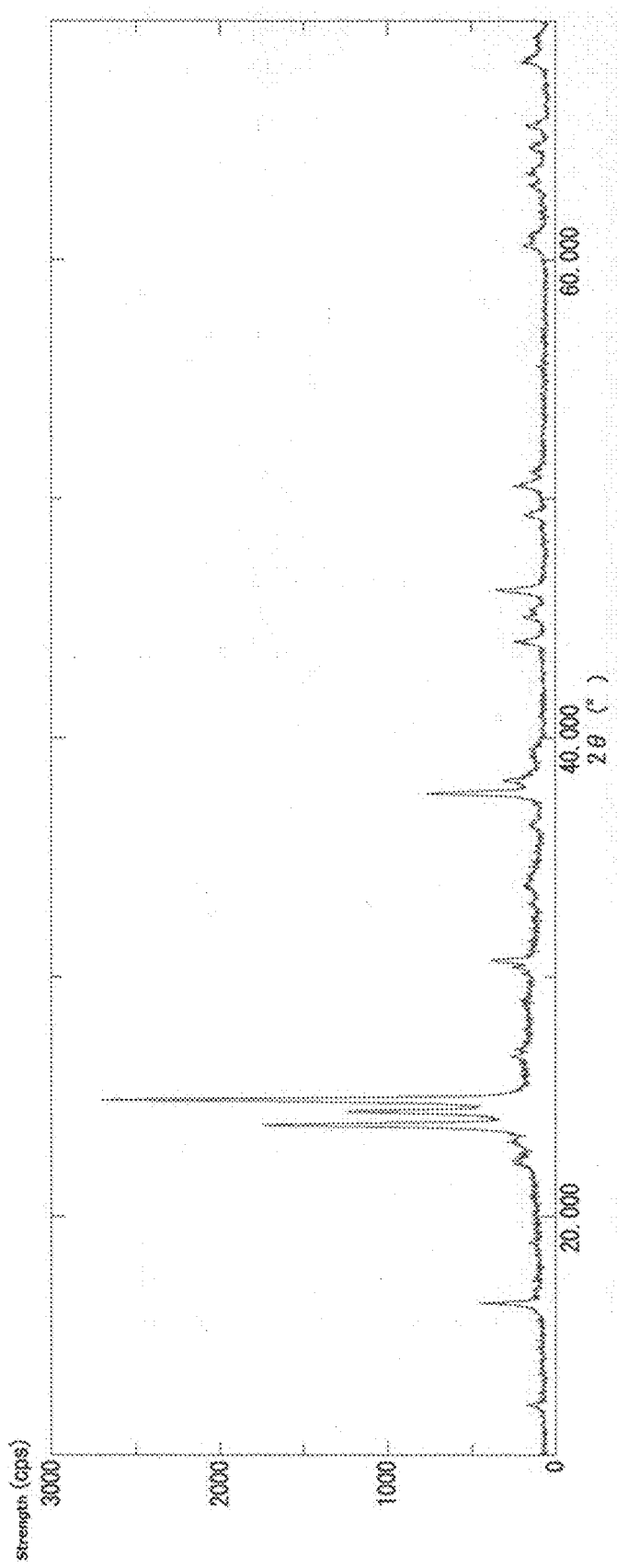
[FIG. 3]

[Fig. 4]
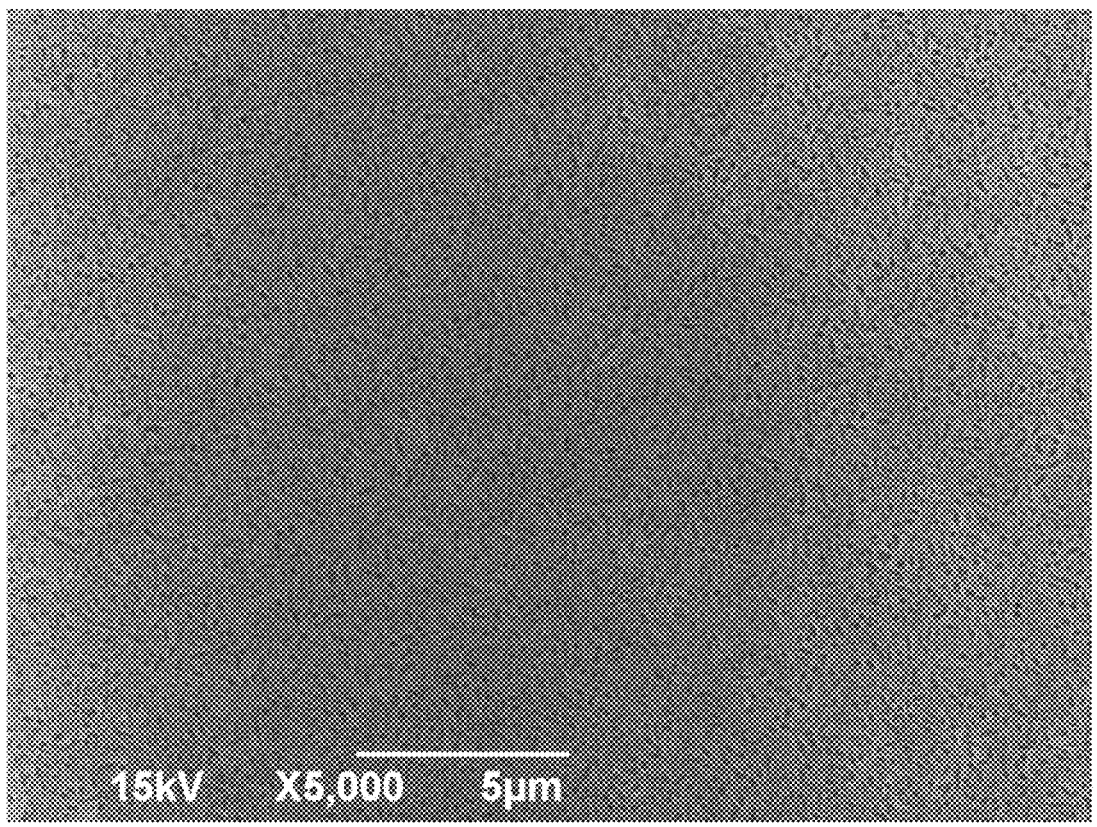

AL$_2$O$_3$-FREE LITHIUM SILICATE GLASS COMPOSITION

TECHNICAL FIELD

The present invention relates to a Al$_2$O$_3$-free lithium silicate glass composition used in the preparation of a ceramic dental crown restorative material used for the aesthetic restorative treatment in the dental field, the glass ceramic obtained by heat treating the Al$_2$O$_3$-free lithium silicate glass composition, and the dental crown restorative material prepared by using the heat treated glass ceramic.

BACKGROUND

In the aesthetic restorative treatment in the dental field, dental crown restorative materials made of ceramics have hitherto been used clinically; however, most of such materials have been glass ceramics including leucite crystals (KAlSi$_2$O$_6$). The refractive index of the leucite crystals approximates to the refractive index of the surrounding glass matrix, accordingly the glass ceramics including the crystals have transparency, and consequently aesthetically excellent dental crown restorative materials have been able to be prepared. However, leucite crystals are dendrites, accordingly cannot suppress the development of cracks generated in the interiors of the glass ceramics, and hence the materials including leucite crystals have been unable to obtain high material strength.

Thus, recently, as glass ceramics to develop high strength, lithium silicate glass ceramics have been applied clinically. The lithium silicate glass ceramics are materials in which by heat treating lithium silicate glass compositions, characteristic forms of crystals (lithium disilicate and/or lithium metasilicate) are precipitated in high densities; and the lithium silicate glass ceramics have a structure in which these crystals are mutually entangled, and accordingly suppress the development of cracks and develop high material strength. At present, the use of these lithium silicate glass ceramics has been expanded to various applications in the dental field; examples of such a use include powdery porcelain materials for building up/burning and ceramic blank for press molding or CAD/CAM mechanical processing. Moreover, many conventional technologies have recently been reported on these lithium silicate glass compositions.

Patent Literature 1 describes the improvement of the material strength by allowing Al$_2$O$_3$ to be included in lithium silicate glass compositions, and thus intentionally also precipitating various crystals (such as lithium aluminum silicate compounds including spodumene) other than the main crystals (lithium disilicate and/or lithium metasilicate).

Patent Literature 2 describes the possibility of the improvement of the transparency, while the material strength is being maintained, by including ZnO in a content of less than 1.0% by weight in the lithium silicate glass composition, and by regulating the ratio between SiO$_2$ and Li$_2$O and the ratio between Al$_2$O$_3$ and K$_2$O.

Patent Literature 3 describes the improvement of the material strength by including Al$_2$O$_3$ and additionally including ZrO$_2$ and TiO$_2$ in the lithium silicate glass composition, and thus intentionally also precipitating various crystals (such as lithium titanium oxide silicate and lithium aluminum silicate compounds including spodumene) other than the main crystals (lithium disilicate and/or lithium metasilicate).

In any of these conventional technologies, a glass composition includes Al$_2$O$_3$ in the lithium silicate glass composition. Al$_2$O$_3$ is a component functioning advantageously in the chemical durability, and accordingly a lithium silicate glass ceramic including Al$_2$O$_3$ develops a high chemical durability, for example, in such a way that the elution the glass components is suppressed when used in the oral cavity, and thus allows a stable glass composition to be constructed. In addition, Al$_2$O$_3$ is one type of glass forming oxide, thus reinforces the glass skeleton and contributes to the improvement of the durability of the glass, and also has an effect to suppress the devitrification (crystal precipitation) in the cooling process when glass blank is prepared.

However, when a lithium silicate glass composition includes Al$_2$O$_3$, in addition to the main crystals (lithium disilicate and/or lithium metasilicate) precipitated from the lithium silicate glass composition, various crystals (such as lithium aluminum silicate compounds including spodumene) are precipitated by heat treatment through the reaction with Li$_2$O in the composition, accordingly the degradation of the material strength is caused, and consequently it is impossible to develop the high material strength demanded for dental glass ceramics. When P$_2$O$_3$ is added as a nucleating agent in the lithium silicate glass composition, Al$_2$O$_3$ and P$_2$O$_3$ in the composition react with each other by heat treatment and crystals such as aluminum phosphate are also precipitated, and hence the addition of P$_2$O$_3$ as a nucleating agent further promotes the degradation of the material strength. Moreover, in lithium silicate glass compositions of conventional technologies, the presence of Al$_2$O$_3$ produces the refractive index difference between such various types of crystals precipitated after heat treatment as described above and the residual glass phase, and consequently in the esthetics of the prepared dental crown restorative material, there has been a significant problem that, for example, lithium silicate glass ceramics after heat treatment become opaque.

In the preparation of the dental crown restorative material by a press method, having hitherto been performed, in which a glass or glass ceramic ingot is pressed into, a phosphate-based investment material is used as a mold. In this case, when Al$_2$O$_3$ is included in the composition of a lithium silicate glass or glass ceramic ingot composed of a lithium silicate glass composition, various crystals (surface reactive layer) such as aluminum phosphate are precipitated, at the time of pressing into, on the surface of the lithium silicate glass ceramics due to the reaction with the phosphate included in the investment material, and hence the degradation of the transparency or material strength is likely to be caused. The reactive layer on the surface of the lithium silicate glass ceramics leads to the surface roughness of the dental crown restorative material, and is a factor to degrade the technical work.

Accordingly, with the conventional lithium silicate glass compositions, it is impossible to efficiently precipitate the main crystals to achieve high strength, due to the effect of Al$_2$O$_3$ included in the composition, and it is impossible to develop the high material strength demanded for the dental glass ceramics because various crystals are precipitated due to the reaction with Li$_2$O or P$_2$O$_3$ in the composition. The precipitation of various crystals leads to a result that the transparency as well as the material strength is adversely affected.

As described above, the ceramic dental crown restorative materials used for the aesthetic restorative treatment in the dental field are demanded to have the mechanical strength capable of withstanding the harsh occlusal pressure or the esthetics analogous to natural tooth; however, as affairs now stands, no lithium silicate glass compositions satisfy these required properties.

RELEVANT REFERENCES

List of Relevant Patent Literature

Patent Literature 1: International Publication No. WO 2012/091201A1
Patent Literature 2: U.S. Pat. No. 8,546,280
Patent Literature 3: Japanese Patent No. 5156031

SUMMARY

As described above, conventional dental lithium silicate glass composition precipitate, by heat treatment in high density, various crystals (lithium disilicate and/or lithium metasilicate) including needle-like forms, and have a structure in which these crystals are mutually entangled, and accordingly suppress the development of cracks and develop high material strength. In such dental lithium silicate glass compositions, for the purpose of improving, for example, the chemical durability, glass stability and transparency, there are found many attempts to mix $Al_2O_3$ in the lithium silicate glass compositions; the $Al_2O_3$ in the composition precipitates, due to the reaction with $Li_2O$ or $P_2O_5$, various crystals other than the main crystals (lithium disilicate and/or lithium metasilicate), and thus suppresses the precipitation and the growth of the main crystals so as to lead to a result that the degradation of the material strength or the transparency is caused.

Accordingly, an object of the present invention is to provide, through the provision of a dental lithium silicate glass composition including a specific $Al_2O_3$-free oxide-containing composition, a dental lithium silicate glass ceramic capable of efficiently precipitating the main crystals (lithium disilicate and/or lithium metasilicate) even after heat treatment, and a dental crown restorative material produced by thermocompression molding, mechanical processing and building up/burning of the dental lithium silicate glass ceramic.

The present inventors made a diligent study in order to achieve the above-described object, and consequently have proposed the present invention by discovering that by preparing a dental lithium silicate glass composition being a dental lithium silicate glass composition having specific oxide content ranges and being free from $Al_2O_3$, various crystals (lithium disilicate and/or lithium metasilicate) including needle-like forms are precipitated efficiently and in a high density after heat treatment, and thus the high strength of the dental lithium silicate glass ceramic can be achieved. In the conventional technologies, for the purpose of improving the glass stability and the chemical durability, $Al_2O_3$ is added; however, in the present invention, for example, $ZrO_2$ functioning as the same glass forming oxide as $Al_2O_3$ is added in place of $Al_2O_3$, and thus, the high strength of the dental lithium silicate glass ceramics has been successfully achieved while the glass stability or the chemical durability is being maintained. Moreover, conventional dental lithium silicate glass ceramics have the refractive index difference between the main crystals (lithium disilicate and/or lithium metasilicate) and the glass matrix surrounding the main crystals, and hence are opaque glass ceramics. In this regard, in the present invention, as glass forming oxide for forming a glass matrix, $ZrO_2$ is used in place of $Al_2O_3$. $ZrO_2$ has a large ionic radius, and thus can increase the refractive index of the glass matrix surrounding the main crystals; accordingly the refractive index difference between the glass matrix and the main crystals is made small, and consequently it has been simultaneously discovered that the transparency of the dental lithium silicate glass ceramic obtained by heat treatment of the dental lithium silicate glass composition can be improved, and thus the present invention has been perfected.

Specifically, the dental lithium silicate glass composition of the present invention is an $Al_2O_3$-free dental lithium silicate glass composition, including the following components:
$SiO_2$: 60.0 to 80.0% by weight
$Li_2O$: 10.0 to 17.0% by weight
$K_2O$: 0.5 to 10.0% by weight
$ZrO_2$: 0.0 to 5.0% by weight
a nucleating agent: 1.0 to 6.0% by weight
a glass stabilizer: 0.0 to 8.0% by weight, and,
a colorant: 0.0 to 10.0% by weight.

It is preferable that the dental lithium silicate glass composition of the present invention includes the following components:
$SiO_2$: 60.0 to 75.0% by weight
$Li_2O$: 12.0 to 17.0% by weight
$K_2O$: 2.0 to 8.0% by weight
$ZrO_2$: 0.1 to 5.0% by weight
a nucleating agent: 1.0 to 5.0% by weight
a glass stabilizer: 0.5 to 7.0% by weight, and,
a colorant: 0.5 to 10.0% by weight.

It is preferable that the dental lithium silicate glass composition of the present invention includes $P_2O_5$ as the nucleating agent.

It is preferable that the dental lithium silicate glass composition of the present invention includes $CeO_2$ as the colorant.

The dental lithium silicate glass ceramic of the present invention is a dental lithium silicate glass ceramic in which by heat treating the dental lithium silicate glass composition of the present invention, lithium metasilicate crystals and/or lithium disilicate crystals are precipitated.

The dental crown restorative material of the present invention is a dental crown restorative material produced from the dental lithium silicate glass ceramic of the present invention by at least one method of thermocompression molding, mechanical processing and building up/firing.

BRIEF DESCRIPTION OF DRAWINGS

FIG. 1 is a graph showing the TG-DTA curve;
FIG. 2 shows the XRD pattern after the first crystallization in Example 1;
FIG. 3 shows the XRD pattern after the second crystallization in Example 1;
FIG. 4 shows the SEM image after the first crystallization in Example 1; and
FIG. 5 is the SEM image after the second crystallization in Example 1.

DETAILED DESCRIPTION OF THE PREFERRED EMBODIMENTS

Hereinafter, the dental lithium silicate glass composition of the present invention is described in detail.

The dental lithium silicate glass composition of the present invention includes the following components, wherein $Al_2O_3$ is not included:

SiO$_2$: 60.0 to 80.0% by weight
Li$_2$O: 10.0 to 17.0% by weight
K$_2$O: 0.5 to 10.0% by weight
ZrO$_2$: 0.0 to 5.0% by weight
a nucleating agent: 1.0 to 6.0% by weight
a glass stabilizer: 0.0 to 8.0% by weight, and,
a colorant: 0.0 to 10.0% by weight.

In the present invention, by adopting such a composition, main crystals (lithium disilicate and/or lithium metasilicate) can be precipitated efficiently and in a high density after heat treatment, and a high strength of the dental lithium silicate glass ceramic can be achieved. The refractive index of the precipitated main crystals (lithium disilicate and/or lithium metasilicate) and the refractive index of the glass phase approximate to each other, and hence the transparency of the dental lithium silicate glass ceramic can also be achieved. In the present invention, an Al$_2$O$_3$-free dental lithium silicate glass composition includes, within the scope of the present invention, not only the case where Al$_2$O$_3$ is not included perfectly, but also even any case where a dental lithium silicate glass composition includes Al$_2$O$_3$ as an impurity within a range of less than 0.1% by weight range, and the advantageous effects of the present invention are exhibited. Accordingly, the analytical measurement method of the Al$_2$O$_3$ content is not particularly limited, but the case where by any one of the heretofore known analytical measurement methods, the Al$_2$O$_3$ content of less than 0.1% by weight is found is included in the category of the dental lithium silicate glass composition of the present invention. That is, the dental lithium silicate glass composition of the present invention is a substantially Al$_2$O$_3$-free dental lithium silicate glass composition, or a dental lithium silicate glass composition including the following components:
SiO$_2$: 60.0 to 80.0% by weight
Li$_2$O: 10.0 to 17.0% by weight
K$_2$O: 0.5 to 10.0% by weight
ZrO$_2$: 0.0 to 5.0% by weight
a nucleating agent: 1.0 to 6.0% by weight
a glass stabilizer: 0.0 to 8.0% by weight
a colorant: 0.0 to 10.0% by weight, and,
Al$_2$O$_3$: 0.0 to 0.1% by weight.

It is preferable that a dental lithium silicate glass composition of the present invention does not include Al$_2$O$_3$ perfectly.

It is also preferable that a dental lithium silicate glass composition of the present invention consists of the following components, wherein Al$_2$O$_3$ is not included:
SiO$_2$: 60.0 to 80.0% by weight
Li$_2$O: 10.0 to 17.0% by weight
K$_2$O: 0.5 to 10.0% by weight
ZrO$_2$: 0.0 to 5.0% by weight
a nucleating agent: 1.0 to 6.0% by weight
a glass stabilizer: 0.0 to 8.0% by weight, and,
a colorant: 0.0 to 10.0% by weight.

The oxide contents of the respective components in the above-described dental lithium silicate glass composition of the present invention are independent of each other, and composed of the following essentially specified components.

The SiO$_2$ included in the dental lithium silicate glass composition of the present invention functions as a glass-forming oxide during glass melting, and after heat treatment, functions as the component of the main crystals (lithium disilicate and/or lithium metasilicate) and a component of the glass phase surrounding the main crystals.

When the SiO$_2$ content in the dental lithium silicate glass composition of the present invention is within a range from 60.0 to 80.0% by weight, SiO$_2$ can be used without causing any problems, and the SiO$_2$ content is more preferably within a range from 60.0 to 75.0% by weight. When the SiO$_2$ content is less than 60.0% by weight, no sufficient glass phase can be formed, the durability of the glass is degraded, the proportion of the main crystals precipitated after heat treatment is concurrently varied, thus no appropriate amount of the main crystals is precipitated, and no high material strength is obtained. In addition, when the SiO$_2$ content is larger than 80.0% by weight, the glass phase is increased to improve the durability of the glass phase, but no sufficient main crystals (lithium disilicate and/or lithium metasilicate) are precipitated, the crystallization of SiO$_2$ as a single substance disturbs the precipitation of the main crystals, and hence no high material strength is obtained.

The Li$_2$O included in the dental lithium silicate glass composition of the present invention functions as a frit during glass melting, promotes the achievement of low-temperature melting of glass, and also functions as a component of the main crystals (lithium disilicate and/or lithium metasilicate) precipitated by heat treatment. When the Li$_2$O content in the dental lithium silicate glass composition of the present invention is within a range from 10.0 to 17.0% by weight, Li$_2$O can be used without causing any problems, and the Li$_2$O content is more preferably within a range from 12.0 to 17.0% by weight.

When the Li$_2$O content is less than 10.0% by weight, the frit is small in amount and glass cannot be melted. In addition, because the proportion of the main crystals to be precipitated after heat treatment is varied, no appropriate amount of the main crystals (lithium disilicate and/or lithium metasilicate) is precipitated, and thus no high material strength is obtained. When the Li$_2$O content is larger than 17.0% by weight, no stable glass phase can be formed, the durability of the glass is degraded, the proportion of the main crystals precipitated after heat treatment is concurrently varied, and no high material strength is obtained.

The K$_2$O included in the dental lithium silicate glass composition of the present invention functions as the frit during glass melting, promotes the low melting of the glass, and concurrently promotes the crystallization of the main crystals (lithium disilicate and/or lithium metasilicate) precipitated by heat treatment. When the K$_2$O content in the dental lithium silicate glass composition of the present invention is within a range from 0.5 to 10.0% by weight, K$_2$O can be used without causing any problems, and the K$_2$O content is more preferably within a range from 2.0 to 8.0% by weight.

When the K$_2$O content is less than 0.5% by weight, namely, the above-described range, the amount of the frit is small, and hence the glass cannot be melted. In addition, the crystallization of the main crystals (lithium disilicate and/or lithium metasilicate) precipitated after heat treatment is suppressed, and hence no high material strength is obtained. When the K$_2$O content is larger than 10.0% by weight, no stable glass phase can be formed, the durability of the glass is degraded, the precipitation of the main crystals precipitated after heat treatment is concurrently disturbed, and hence no high material strength is obtained.

The ZrO$_2$ included in the dental lithium silicate glass composition of the present invention functions as a glass-forming oxide during glass melting, does not undergo any change after heat treatment, and contributes to the stabilization of the glass phase.

ZrO$_2$ can increase the refractive index of the glass phase, accordingly the refractive index of the glass phase and the refractive index of the crystal phase can be allowed to approximate to each other, and thus $ZrO_2$ contributes to the improvement of the transparency. When the $ZrO_2$ content in the dental lithium silicate glass composition of the present invention is within a range from 0.0 to 5.0% by weight, $K_2O$ can be used without causing any problems, and the $ZrO_2$ content is more preferably within a range from 0.1 to 5.0% by weight.

When the $ZrO_2$ content is larger than 5.0% by weight, the durability is improved with the increase of the glass phase; however, during heat treatment, no sufficient main crystals (lithium disilicate and/or lithium metasilicate) are precipitated, the crystallization of $ZrO_2$ as a single substance disturbs the precipitation of the main crystals, and hence no high material strength is obtained.

It is possible to use, without being particularly limited, any nucleating material included in the dental lithium silicate glass composition of the present invention, functioning as a generation origin of the main crystals (lithium disilicate and/or lithium metasilicate) precipitated by heat treatment. Specific examples of these nucleating agents include: $P_2O_3$, $TiO_2$, $WO_3$, $V_2O_3$, Pt and Ag. Among these nucleating agents, a particularly effective nucleating agent is $P_2O_3$. At least one of these nucleating agent is mixed, but combinations of two or more of these can also be mixed. By using $P_2O_3$ as the nucleating agent, it may be possible to deposit a fine $Li_3PO_4$ (lithium phosphate) which acts as the origin of the main crystals (lithium disilicate and/or lithium metasilicate), therefore it may be possible to deposit the main crystals (lithium disilicate and/or lithium metasilicate) effectively.

When the nucleating agent content in the dental lithium silicate glass composition of the present invention is within a range from 1.0 to 6.0% by weight, the nucleating agent can be used without causing any problems, and the nucleating agent content is more preferably within a range from 1.0 to 5.0% by weight. When the nucleating agent content is less than 1.0% by weight, the coarsening of the main crystals and the degradation of the transparency are caused, and no sufficient transparency and no high material strength can be obtained. When the nucleating agent content is larger than 6.0% by weight, the increase of the crystal amount and the refinement of the crystal are promoted, but the glass phase remaining after the crystallization is decreased, and thus the durability of the glass is degraded.

It is possible to use, without being particularly limited, any glass stabilizer included in the dental lithium silicate glass composition of the present invention, being a glass phase conditioner and functioning for the improvement of the stability and the durability of the glass phase. Specific examples of these glass stabilizers include: CaO, MgO, SrO, BaO, ZnO, $Y_2O_3$, $Ta_2O_5$, $Sb_2O_3$, $GeO_2$ and $B_2O_3$. If necessary, one of these glass stabilizers or combinations of two or more of these glass stabilizers can also be mixed. When the glass stabilizer content in the dental lithium silicate glass composition of the present invention is within a range from 0.0 to 8.0% by weight, the glass stabilizer can be used without causing any problems, and the glass stabilizer content is more preferably within a range from 0.5 to 7.0% by weight.

When the glass stabilizer content is larger than 8.0% by weight, the glass phase is stable, the durability is improved, but the precipitation of the main crystals (lithium disilicate and/or lithium metasilicate) is disturbed, and hence no high material strength is obtained.

It is possible to use, without being particularly limited, any colorant included in the dental lithium silicate glass composition of the present invention, functioning as a color tone conditioner for approximating to natural teeth (dentin and enamel). Specific examples of these colorants include: MnO, $Fe_2O_3$, $Tb_4O_7$, $Eu_2O_3$, $Ni_2O_3$, $CO_2O_3$, $Cr_2O_3$, $SnO_2$, $CeO_2$, $Nd_2O_3$, $Pr_6O_{11}$, $Sm_2O_3$, $V_2O_5$, $Dy_2O_3$, $Ho_2O_3$ and $Er_2O_3$. In addition, natural teeth exhibit fluorescent colors by the irradiation of ultraviolet light, and accordingly, it is further preferable that these colorants exhibit fluorescent colors. Further, because $CeO_2$ acts the yellow coloring component which may be used for reproducing a tooth crown color, it is preferable that the dental lithium silicate glass composition of the present invention includes $CeO_2$ as a colorant. These colorants can be appropriately selected according to the color tone of the dental crown restorative material, and if necessary, one or combinations of two or more thereof can be mixed.

When the colorant content in the dental lithium silicate glass composition of the present invention is within a range from 0.0 to 10.0% by weight, the colorant can be used without causing any problems, and the colorant content is more preferably within a range from 0.5 to 10.0% by weight. When the contents of these colorants are each larger than 10.0% by weight, an abundant color tone conditioning can be performed, but the precipitation of the main crystals (lithium disilicate and/or lithium metasilicate) is disturbed, and hence no high material strength is obtained.

The method for producing the dental lithium silicate glass composition of the present invention is not particularly limited, and any production method can produce the foregoing dental lithium silicate glass composition. Specific examples of the production method concerned include: a method in which the glass raw materials are mixed, and then melted at a high temperature, and a method (sol-gel method) in which organic compounds or inorganic compounds are dissolved in a solvent, and are allowed to react in the resulting solution; it is preferable to use the glass melting method from the viewpoint of the easiness of the glass composition design, the production amount, the production facilities, the cost and others. The production conditions in the glass melting method, such as the feeding temperature of the glass raw materials, the temperature increase rate, the melting temperature and the holding time are not particularly limited; as long as the production conditions allow to obtain a melt in which the glass materials are uniformly melted, the production conditions are not particularly limited. In particular, the dental lithium silicate glass composition of the present invention is preferably melted within a range from 1200° C. to 1650° C.

Moreover, the dental lithium silicate glass composition of the present invention is not particularly limited with respect to the shape thereof, and can be regulated so as to have various shapes such as a powdery shape, a granular shape, a plate-like shape (frit) and a glass block shape (glass blank). The glass block shape (glass blank) can be produced by casting the above-described melt into, for example, a carbon, metal or ceramic mold, and by slowly cooling the melt down to room temperature.

The glass blank (columnar shape or prismatic shape) can also be molded by filling under pressurization the glass melt into a mold in a high viscosity state (at a temperature of 700° C. to 1200° C.) achieved by controlling the viscosity of the glass melt. A plate-like shape (frit) can be produced by dropping the above-described melt between internally cooled two rolls and thus by rapidly cooling the melt. The granular shape can be produced by placing in a whirling manner the above-described melt into cooled running water. The powdery shape can be obtained by pulverizing these shapes by using, for example, a pulverizer. The shapes of the dental lithium silicate glass composition can be appropriately regulated, for example, by the production method based on the heat treatment as the subsequent step, or by the production method in the case of the production of a dental crown restorative material.

As a feature of the present invention, the present invention is capable of producing dental lithium silicate glass ceramics by efficiently and highly densely precipitating the main crystals (lithium disilicate and/or lithium metasilicate) through the heat treatment of the dental lithium silicate glass compositions having various shapes. The heat treatment is an important step because the heat treatment can control the precipitation proportion of the main crystals (lithium disilicate and/or lithium metasilicate) precipitated after the heat treatment. The heat treatment conditions for heat treating the dental lithium silicate glass composition of the present invention, such as the heat treatment starting temperature, the temperature increase rate, the heat treatment temperature, the heat treatment holding time, and the annealing temperature are not particularly limited, and can be appropriately selected according to, for example, the shape of the dental lithium silicate glass composition to be heat treated, the method for producing a dental crown restorative material, and the control of the precipitation conditions of the crystals. Among these, the heat treatment temperature is a particularly important item because of being capable of controlling the precipitation proportion of the main crystals (lithium disilicate and/or lithium metasilicate), and the heat treatment is preferably performed at a heat treatment temperature falling within a range from 500 to 1000° C. When the heat treatment temperature is lower than 500° C., the dental lithium silicate glass composition of the present invention cannot be fired or crystallized. When the heat treatment temperature is equal to or higher than 1000° C., the forms of the precipitated main crystals are collapsed due to the nature of the dental lithium silicate glass composition of the present invention. Accordingly, the heat treatment temperature should not deviate from this temperature range.

On the other hand, preferably, the heat treatment starting temperature is 500° C. to 550° C., the temperature increase rate is 10° C. to 20° C./min, and the annealing rate is 10° C. to 20° C./min. The starting temperature of the heat treatment is preferably in the vicinity of the glass transition point for the purpose of appropriately precipitating the main crystals. The temperature increase rate is preferably such that the temperature is more slowly increased because the crystallization is required to be more stably promoted. The annealing rate has little effect on the crystal precipitation; however, when a rapid cooling is performed, cracks might occur in the glass, and hence a slow cooling is preferable.

The lithium metasilicate crystal precipitated from the dental lithium silicate glass composition of the present invention has a tendency to be precipitated within a heat treatment temperature range from 580° C. to 780° C., the crystal is very fine and has various crystal forms, and hence the dental lithium silicate glass composition has the features that the material strength and the ductility are both low and the processability is excellent. On the other hand, the lithium disilicate crystal precipitated from the dental lithium silicate glass composition of the present invention has a tendency to be precipitated within a heat treatment temperature range from 800° C. to 920° C., this crystal has a large size as compared with the above-described lithium metasilicate crystal and exhibits a needle-like form, these crystals are precipitated in a high density and have a structure in which these crystals are entangled with each other, and hence the dental lithium silicate glass composition has the features that the development of the cracks is suppressed and the material strength is developed. The precipitation temperature of the crystal precipitated from the dental lithium silicate glass composition of the present invention can be verified from the exothermic peak of the TG-DTA, and the crystal can be identified by X-ray diffraction.

It is also an effective method to regulate the holding time within the heat treatment temperature range allowing the above-described respective crystals (lithium disilicate and lithium metasilicate) to be precipitated, for the purpose of efficiently precipitate these crystals in high densities. Specifically, as the heat treatment of the dental lithium silicate glass composition of the present invention, preferable is a two-stage heat treatment in which the composition is held for a certain period of time at the heat treatment temperature allowing the lithium metasilicate to be precipitated, then the temperature is slowly increased to the heat treatment temperature allowing the lithium disilicate to be precipitated and the composition is held for a certain period of time, then the composition is slowly cooled; it is more preferable to perform a three-stage heat treatment including before such a two-stage treatment, a nucleation heat treatment performing a holding for a certain period of time within a range from 500° C. to 550° C. The nucleation heat treatment aims at the formation of the generation origin of the main crystals precipitated from the dental lithium silicate glass composition of the present invention, and is an effective method for precipitating the crystals efficiently and in a high density. When $P_2O_3$ is included as the nucleating agent in the dental lithium silicate glass composition of the present invention, $Li_3PO_4$ is sometimes precipitated as a subcrystal when the heat treatment is performed; however, such a subcrystal falling within the composition range in the dental lithium silicate glass composition of the present invention causes no problem.

There is no particular limitation on the shape of the dental lithium silicate glass ceramic produced by precipitating the main crystals (lithium disilicate and/or lithium metasilicate) through the heat treatment of the dental lithium silicate glass composition of the present invention; the shape of the dental lithium silicate glass ceramic can be selected according to the step for producing the dental crown restorative material. For example, an agglomerated state is taken by the dental lithium silicate glass ceramic allowed to precipitate the main crystals (lithium disilicate and/or lithium metasilicate) by heat treating a powdery, granular or plate-like dental lithium silicate glass composition; however, by pulverization processing of these agglomerates, a powdery dental lithium silicate glass ceramic can be produced. The average particle size of the resulting powdery ceramic is 1 to 100 μm, and preferably 10 to 50 μm. The powdery dental lithium silicate glass composition is filled in a mold and compressed to form a molded article (columnar shape or prismatic shape), the molded article is heat treated to precipitate the main crystals (lithium disilicate and/or lithium metasilicate), and thus a blank (columnar shape or prismatic shape) of the dental lithium silicate glass ceramic can be produced. Moreover, the glass blank (columnar shape or prismatic shape) of the dental lithium silicate glass composition is not pulverized and heat treated as it is, consequently the main crystals (lithium disilicate and/or lithium metasilicate) are precipitated, and thus a blank (columnar shape or prismatic shape) of the dental lithium silicate glass ceramic can be produced. As described above, the dental lithium silicate glass composition of the present invention is molded into various shapes, the resulting various shapes are heat treated, and thus the dental lithium silicate glass ceramics having various shapes can be produced; however, the shapes of the dental lithium silicate glass ceramics are not limited to such shapes as described above.

From the dental lithium silicate glass ceramic obtained by heat treating the dental lithium silicate glass composition, it is possible to produce a dental crown restorative material by at least one production method of thermocompression molding, mechanical processing and building up/firing. For example, a powdery heat-treated dental lithium silicate glass ceramic is mixed with a malaxation liquid, then the resulting mixture is built up on a base while the mixture is being condensed, thus a form of the dental crown restorative material is reproduced and then fired, and consequently a dental crown restorative material can be produced. The blank of the dental lithium silicate glass ceramic obtained by heat treatment is softened by using a special press molding device under heating and pressurization conditions, then the blank is pressed into a mold deprived of wax by firing, and thus a dental crown restorative material can be produced. Moreover, the blank of the dental lithium silicate glass ceramic obtained by heat treatment is subject to cutting and machining by using a computer-controlled cutting and machining machine, and thus a dental crown restorative material can also be produced.

In these production methods, by taking advantage of the features of the main crystals (lithium metasilicate and lithium disilicate) precipitated from the above-described dental lithium silicate glass composition of the present invention and the differences in the precipitation temperatures of the respective crystals, the dental crown restorative material can be efficiently produced in each of the production methods; this is also a feature. In particular, a production method is effective in the production of the dental crown restorative material by machining; specifically, effective is a production method in which: a dental lithium silicate glass ceramic having lithium metasilicate crystals mainly precipitated is machined into a desired shape of the dental crown restorative material; and then the machined dental crown restorative material is again heat treated to precipitate lithium disilicate crystals to achieve a high strength.

In addition, when conventional dental lithium silicate glass ceramics are softened by heating and pressed into an investment material mold, the conventional dental ceramics undergo a reaction with the investment material; consequently, various crystals (surface reaction layer) such as aluminum phosphate ($AlPO_4$) are precipitated on the surface of the produced dental crown restorative material to generate surface roughness, and thus technical work is degraded. However, the dental lithium silicate glass ceramics obtained by heat treating the dental lithium silicate glass composition of the present invention does not include $Al_2O_3$ and is accordingly improved in the chemical stability, hence the precipitation of the crystals (such as aluminum phosphate ($AlPO_4$)) due to the reaction with the investment material does not occur, and as a feature of the dental lithium silicate glass ceramics, smooth and shiny surface properties are obtained.

Hereinafter, there are shown specific examples of a series of processes from the production of the dental lithium silicate glass composition of the present invention, through the production of the dental lithium silicate glass ceramic obtained by heat treating the glass composition, to the production of the dental crown restorative material using the dental lithium silicate glass ceramic; however, the production of the dental lithium silicate glass composition of the present invention, the dental lithium silicate glass ceramic and the dental crown restorative material is not limited to these examples.

Production Process 1:

1-A Step: Production of a Dental Lithium Silicate Glass Composition (1-A-1) A step in which the glass raw materials (carbonates/oxides and colorant oxide) are mixed, and then the resulting mixture is melted in a temperature range from 1200° C. to 1650° C.

(1-A-2) A step in which the molten glass melt is filled as it is in a mold, and a glass blank (columnar shape or prismatic shape) is formed.

1-B Step: Production of a Dental Lithium Silicate Glass Ceramic (1-B-1) A step in which the glass blank is heat treated at least once in a range from 500° C. to 950° C.

1-C Step: Production of a Dental Crown Restorative Material (1-C-1) A step in which the lithium silicate glass ceramic of the heat-treated glass blank is heated and softened at a temperature of 500° C. to 1200° C., then pressed into the clearance of the investment material mold under a pressure of approximately 0.1 to 1 MPa, and thus a dental crown restorative material having a desired form (bridge or crown) is produced.

Production Process 2:

2-A Step: Production of a Dental Lithium Silicate Glass Composition (2-A-1) A step in which the glass raw materials (carbonates/oxides and colorant oxide) are mixed, then the resulting mixture is melted in a temperature range from 1200° C. to 1650° C.

(2-A-2) A step in which the molten glass melt is filled as it is in a mold, and a glass blank (columnar shape or prismatic shape) is formed.

2-B Step: Production of a Dental Lithium Silicate Glass Ceramic (2-B-1) A step in which the glass blank is at least once heat treated in a range from 500° C. to 780° C.

2-C Step: Production of a Dental Crown Restorative Material (2-C-1) A step in which the lithium silicate glass ceramic of the heat treated glass blank is subject to cutting and machining by using a computer-controlled cutting and machining to prepare a desired form (bridge or crown), the cut and machined article is at least once heat treated in a temperature range from approximately 700° C. to 950° C. for between approximately 5 to 30 minutes, and thus a dental crown restorative material is produced.

Production Process 3:

3-A Step: Production of a Dental Lithium Silicate Glass Composition (3-A-1) A step in which the glass raw materials (carbonate/oxide) are mixed, and then the resulting mixture is melted in a temperature range from 1200° C. to 1650° C.

(3-A-2) A step in which the molten glass melt is cooled, and thus a granular glass material or a glass plate (frit) is formed.

3-B Step: Production of a Dental Lithium Silicate Glass Ceramic (3-B-1) A step in which the granular glass material or the glass plate is heat treated at least once in a range from 500° C. to 780° C.

(3-B-2) A step in which the heat treated granular glass material or the heat treated glass plate is pulverized to a powder having an average particle size of 10 to 50 μm.

(3-B-3) A step in which the pulverized powder and the colorant oxide are mixed.

(3-B-4) A step in which the above-described mixture powder is packed in a mold having a desired shape, and thus a molded article, a glass blank having a non-uniform structure, is formed.

(3-B-5) A step in which the molded article is subjected to a heat treatment in a temperature range from 400° C. to 950° C. under vacuum, and thus a dense glass ceramic blank is formed.

3-C Step: Production of a Dental Crown Restorative Material (3-C-1) A step in which the lithium silicate glass ceramic having a blank shape is heated and softened at a temperature of 500° C. to 1200° C., then pressed into the clearance of the investment material mold under a pressure of approximately 0.1 to 1 MPa, and thus a dental crown restorative material having a desired form (bridge or crown) is produced.

Production Process 4:

4-A Step: Production of a Dental Lithium Silicate Glass Composition (4-A-1) A step in which the glass raw materials (carbonates/oxides) are mixed, and then the resulting mixture is melted in a temperature range from 1200° C. to 1650° C.

(4-A-2) A step in which the molten glass melt is cooled, and thus a granular glass material or a glass plate (frit) is formed.

4-B Step: Production of a Dental Lithium Silicate Glass Ceramic (4-B-1) A step in which the granular glass material or the glass plate (frit) is heat treated at least once in a range from 500° C. to 780° C.

(4-B-2) A step in which the heat treated granular glass material or the heat treated glass plate (frit) is pulverized to a powder having an average particle size of 10 to 50 μm.

(4-B-3) A step in which the pulverized powder and the colorant oxide are mixed.

(4-B-4) A step in which the above-described mixture powder is packed in a mold having a desired shape, and thus a molded article, a glass blank having a non-uniform structure, is formed.

(4-B-5) A step in which the molded article is subjected to a heat treatment in a temperature range from 400° C. to 950° C. under vacuum, and thus a dense glass ceramic blank is formed.

4-C Step: Production of a Dental Crown Restorative Material (4-C-1) A step in which the lithium silicate glass ceramic having a blank shape is subject to cutting and machining by using a computer-controlled cutting and machining machine to prepare a desired form (bridge or crown), the cut and machined article is at least once heat treated in a temperature range from approximately 700° C. to 950° C. for between approximately 5 to 30 minutes, and thus a dental crown restorative material is produced.

Production Process 5:

5-A Step: Production of a Dental Lithium Silicate Glass Composition (5-A-1) A step in which the glass raw materials (carbonates/oxides and colorant oxide) are mixed, and then the resulting mixture is melted in a temperature range from 1200° C. to 1650° C.

(5-A-2) A step in which the molten glass melt is cooled, and thus a granular glass material or a glass plate (frit) is formed.

5-B: Production of a Dental Lithium Silicate Glass Ceramic (5-B-1) A step in which the granular glass material or the glass plate (frit) is heat treated at least once in a range from 500° C. to 780° C.

(5-B-2) A step in which the heat treated granular glass material or the heat treated glass plate (frit) is pulverized to a powder having an average particle size of 10 to 50 μm.

(5-B-3) A step in which the pulverized powder and the colorant oxide are mixed.

5-C Step: Production of a Dental Crown Restorative Material (5-C-1) A step in which the dental lithium silicate glass ceramic, a powder after heat treatment, mixed with a colorant, is mixed with a malaxation liquid; then the resulting mixture is built up on a base prepared from a zirconia and lithium silicate-based glass ceramic while the mixture is being condensed; and the built-up mixture is fired by using a firing furnace in a range from 500° C. to 950° C.; and thus a dental crown restorative material, having a desired form (bridge or crown) is produced.

The above-described dental crown restorative material (such as a bridge or a crown) produced from the dental lithium silicate glass ceramic can be finished with a color tone approximating to the natural teeth and aesthetically, by finally performing a coloration with a staining material or the coating of the surface layer with a coating material. Examples of such a staining material and such a coating material include, without being limited to: a ceramic, a sintered ceramic, a glass ceramic, a glass, a glaze and/or composite materials. The staining material is used as a color tone conditioner for mimicking the color tone of the natural teeth, and the coating material is used for improving the smoothness and shine and the glossiness of the surface. Among these staining materials and these coating materials, preferable are the staining materials and the coating materials capable of being fired in a temperature range from 650° C. to 950° C., and having the coefficient of thermal expansion difference, from the coefficient of thermal expansion of the dental crown restorative material prepared from the lithium silicate glass ceramic of the present invention, falling within a range of $1.0 \pm 0.5 \times 10^{-6}$ $K^{-1}$.

As described above, the dental lithium silicate glass ceramic appropriately formed by using the dental lithium silicate glass composition of the present invention can serve as various dental crown restorative materials, to be used clinically, such as an inlay, an onlay, a crown, a bridge, a post, a facing crown, a jacket crown, a laminate veneer and splinted crowns.

EXAMPLES

The present invention is described in dental on the basis of following Examples. However, the present invention is not limited to the scope of these Examples.

The test methods adopted in Examples and Comparative Examples are as follows.

[Evaluation Methods]

(1) Bending Strength (Three-Point Bending) Test

The bending strength test was performed according to ISO 6872 Dentistry-Ceramic Materials.

(2) Solubility Test

The solubility test was performed according to ISO 6872 Dentistry-Ceramic Materials.

(3) Contrast Ratio Measurement

Round plates (φ14.0 mm×2.0 mm) were prepared by using the dental lithium silicate glass ceramics of respective Examples and Comparative Examples; samples regulated to be 1 mm in thickness were subjected to a color measurement (white background and black background) by using a spectrocolorimeter, and the contrast ratios were calculated from the color measurement data.

(Contrast ratio)=(Y value of black background colorimetry)/(Y value of white background colorimetry)  Calculation formula:

Measurement apparatus: CM-3500d (manufactured by Konica Minolta Holdings, Inc.)

(4) Verification of Crystal System

The dental lithium silicate glass ceramics of respective Examples and Comparative Examples were pulverized, and the crystal systems of the crystals precipitated in the heat treatments of the respective stages were verified by XRD. The abbreviations in the table mean as follows: LDS: lithium disilicate, LMS: lithium metasilicate, and LP: lithium phosphate.

Apparatus used: Multiflex (Rigaku Corp.)
Measurement condition: Scanning range 10° to 70°, scanning speed: 2.0°/min (5) Test of Seizure to Investment Material By using the dental lithium silicate glass ceramics of respective Examples and Comparative Examples, blanks were softened under heated and pressurized condition, and then pressed, by using a press molding apparatus, into a mold from which a round plate (φ14.0 mm×2.0 mm) made of a wax was removed by firing, and thus the specimens were prepared. Subsequently, the investment material of each of the press molded specimens was removed with a alumina sand blast (alumina particle size: 110 μm, pressure: 0.4 MPa), the surface of each of the specimens after removal of the investment material was visually observed, and thus the removal state of the investment material was evaluated.

Investment material: Ceravety Press & Cast (manufactured by Shofu Inc.)

Press molding apparatus: Estemat Press (manufactured by Shofu Inc.)

[Crystal Heat Treatment Temperature]

First, the precipitation temperature (lithium disilicate and lithium metasilicate) of the dental lithium silicate glass composition of the present invention is specified by the precipitation temperature of the main crystals (lithium disilicate and lithium metasilicate) precipitated in Example 1.

The dental lithium silicate glass composition described in Table 1: The glass raw material mixture corresponding to Example 1 was maintained at 1450° C. for 1 hour to be melted. The resulting glass melt was filled in a carbon mold (φ12 mm×10 mm) preheated to 500° C., and thus a glass blank, the dental lithium silicate glass composition of the present invention, was prepared. The resulting glass blank was transparent and uniform.

In order to verify the crystal precipitation temperature of the glass blank, a TG-DTA measurement (measurement conditions: 25° C. to 1000° C. (temperature increase rate: 10° C./min)) was performed (FIG. 1). Consequently, exothermic peaks due to crystal precipitation were verified at 642° C. and 805° C. Next, the glass blank was heat treated at the temperatures of the respective exothermic peaks (starting temperature: 500° C., temperature increase rate: 10° C./min, firing temperatures: temperatures of exothermic peaks 642° C. and 805° C.), and thus the dental lithium silicate glass ceramics of the present invention were prepared and were measured by XRD. From the obtained XRD pattern results, it was verified that the lithium metasilicate crystal was precipitated at 642° C. (FIG. 2), and the lithium disilicate crystal was precipitated at 805° C. (FIG. 3).

FIG. 4 shows an electron microscope observation image of the dental lithium silicate glass ceramic of the present invention heat treated at 642° C., after being subjected to an etching with 1% hydrofluoric acid for 30 seconds. From FIG. 4, it was able to be verified that the lithium metasilicate crystals disappeared due to the etching and fine traces (vacancies) of crystals were observed.

FIG. 5 shows an electron microscope observation image of the dental lithium silicate glass ceramic heat treated at 805° C., and subjected to an etching with 1% hydrofluoric acid for 3 minutes. From FIG. 5, it was able to be verified that the glassy portion disappeared, and the needle-like crystals derived from lithium disilicate were observed.

The main crystals were precipitated by subjecting, on the basis of the above-described method, the glass obtained from the dental lithium silicate glass composition of the present invention to a heat treatment (first crystallization heat treatment (precipitation of lithium metasilicate): 650° C., second crystallization heat treatment (precipitation of lithium disilicate): 850° C.)

(Test by Press Molding)

The dental lithium silicate glass compositions, Examples 1 to 31, described in Tables 1 to 5 and the glass raw material mixtures corresponding to Comparative Examples 1 to 14, described in Tables 6 to 8 were maintained at 1450° C. for 1 hour to be melted. The resulting glass melts were each filled in a carbon mold (φ12 mm×10 mm) preheated to 500° C., and thus glass blanks of the dental lithium silicate glass compositions of Examples 1 to 31 and the glass blanks of Comparative Examples 1 to 14 were prepared. The resulting glass blanks were each heat treated (generation of crystal nuclei) at 500° C. for 10 minutes, then subjected to a heat treatment (first crystallization heat treatment) at 650° C. for 20 minutes, and further subjected to a heat treatment (second crystallization heat treatment) at 850° C. for 10 minutes. The glass ceramics prepared by the three staged heat treatment were used as the glass ceramic blanks for press molding.

The wax having the same shape as the shapes of the specimens used in the above-described evaluation tests (1) to (3) was embedded in the investment material (Ceravety Press & Cast, manufactured by Shofu Inc.), and the hardened mold was fired at 850° C. for 1 hour to remove the wax. In the mold after firing treatment, each of the produced glass ceramic blanks was inserted, and was subjected to a press molding (press starting temperature: 700° C., press temperature: 910° C., holding time: 15 minutes, temperature increase rate: 60° C./min, press time: 3 minutes) by using a press molding apparatus (Estemat Press, manufactured by Shofu Inc.). The mold was cooled, then each of the specimens was dug out by a sand blast treatment, the size of each of the specimens was regulated, and the above-described evaluation tests (1) to (3) were performed. In addition, when the specimens were dug out, the above-described evaluation test (5) was also performed in order to verify the condition of the seizure to the investment material. The above-described evaluation test (4) was performed in order to verify the crystal system in the final specimen.

(Test by Machining)

The dental lithium silicate glass compositions, Examples 1 to 31, described in Tables 1 to 5 and the glass raw material mixtures corresponding to Comparative Examples 1 to 14, described in Tables 6 to 8 were maintained at 1450° C. for 1 hour to be melted. The resulting glass melts were each filled in a carbon casting mold (5 mm×22 mm×22 mm) preheated to 500° C., and thus glass blanks of the dental lithium silicate glass compositions of Examples 1 to 31 and the glass blanks of Comparative Examples 1 to 14 were prepared. The resulting glass blanks were each heat treated (generation of crystal nuclei) at 500° C. for 10 minutes, and then subjected to a heat treatment (first crystallization heat treatment) at 650° C. for 20 minutes; the glass ceramics produced by this two-stage heat treatment were used as the glass ceramic blanks for performing the machining.

The glass ceramic blanks were cut and machined by using a dental CAD/CAM system into the same shapes as the shapes of the specimens used in the above-described evaluation tests (1) to (3), then further subjected to a heat treatment (second crystallization heat treatment, the starting temperature: 700° C., firing temperature: 850° C., holding time: 10 minutes, temperature increase rate: 60° C./min), and thus specimens were prepared; the sizes of the specimens were regulated, and then the above-described evaluation tests (1) to (3) were performed. The above-described evaluation test (4) was also performed in order to verify the crystal system in the final specimen.

(Test by Powder Molding)

The dental lithium silicate glass compositions, Examples 1 to 31, described in Tables 1 to 5 and the glass raw material mixtures corresponding to Comparative Examples 1 to 14, described in Tables 6 to 8 were maintained at 1450° C. for 1 hour to be melted. The resulting glass melts were each filled in a carbon casting mold (5 mm×22 mm×22 mm) preheated to 500° C., and thus glass blanks of the dental lithium silicate glass compositions of Examples 1 to 31 and the glass blanks of Comparative Examples 1 to 14 were prepared. The resulting glass blanks were each heat treated (generation of crystal nuclei) at 500° C. for 10 minutes, and then subjected to a heat treatment (first crystallization heat treatment) at 650° C. for 20 minutes; the dental lithium silicate glass ceramic blanks of the present invention produced by this two-stage heat treatment were obtained.

The glass ceramic blanks were each pulverized to yield a glass ceramic powder having an average particle size of 20 µm. Each of these powders was malaxated with distilled water into a slurry; each of the resulting slurries was poured into a silicon mold having the same shape as the shape of the specimen used in each of the above-described evaluation tests (1) to (3). After the moisture of each of the poured slurries was sufficiently removed, each of the molded article was released from the silicon mold, and subjected to a heat treatment (heat treatment starting temperature: 500° C., heat treatment ending temperature: 950° C., temperature increase rate: 10° C./min), and thus specimens were prepared; the sizes of the specimens were regulated, and then the above-described evaluation tests (1) to (3) were performed. The above-described evaluation test (4) was performed in order to verify the crystal system in the final specimen.

[Examples]

TABLE 1

| | Component | Example 1 | Example 2 | Example 3 | Example 4 | Example 5 | Example 6 |
|---|---|---|---|---|---|---|---|
| Mass Ratio (%) | $SiO_2$ | 67.5 | 71.6 | 70.4 | 70.6 | 69.8 | 67.5 |
| | $Li_2O$ | 15.0 | 15.9 | 15.7 | 15.7 | 15.5 | 15.0 |
| | $K_2O$ | 4.4 | 4.7 | 4.6 | 4.6 | 4.6 | 4.4 |
| | $ZrO_2$ | 3.4 | 3.6 | 3.5 | 3.6 | 3.5 | 3.4 |
| | $P_2O_5$ | 4.0 | 4.2 | 4.2 | 4.2 | 4.1 | 4.0 |
| | ZnO | 1.9 | — | — | 1.3 | — | 1.8 |
| | SrO | 1.5 | — | 1.6 | — | — | — |
| | BaO | — | — | — | — | — | 1.5 |
| | $CeO_2$ | 2.3 | — | — | — | 2.5 | 2.4 |
| | Total | 100.0 | 100.0 | 100.0 | 100.0 | 100.0 | 100.0 |
| Test Result of Press Molding | Bending Strength (MPa) | 450 | 454 | 477 | 392 | 490 | 454 |
| | Solubility (µg/cm$^2$) | 25 | 34 | 42 | 37 | 40 | 45 |
| | Contrast Ratio | 0.25 | 0.48 | 0.46 | 0.38 | 0.41 | 0.28 |
| | Crystal System | LDS, LP | LDS, LP | LDS, LP | LDS, LP | LDS, LMS, LP | LDS, LP |
| | Seizure to Investment Material | Good | Good | Good | Good | Good | Good |
| Test Result of Machining | Bending Strength (MPa) | 440 | 437 | 465 | 400 | 452 | 450 |
| | Solubility (µg/cm$^2$) | 30 | 40 | 40 | 32 | 47 | 30 |
| | Contrast Ratio | 0.30 | 0.42 | 0.40 | 0.42 | 0.38 | 0.30 |
| | Crystal System | LDS, LMS, LP | LDS, LMS, LP | LDS, LMS, LP | LDS, LMS, LP | LDS, LMS, LP | LDS, LMS, LP |
| Test Result of Powder Molding | Bending Strength (MPa) | 380 | 375 | 395 | 370 | 405 | 377 |
| | Solubility (µg/cm$^2$) | 40 | 42 | 43 | 49 | 52 | 40 |
| | Contrast Ratio | 0.35 | 0.47 | 0.43 | 0.48 | 0.40 | 0.38 |
| | Crystal System | LDS, LMS, LP | LDS, LMS, LP | LDS, LMS, LP | LDS, LMS, LP | LDS, LMS, LP | LDS, LMS, LP |

TABLE 2

| | Component | Example 7 | Example 8 | Example 9 | Example 10 | Example 11 | Example 12 |
|---|---|---|---|---|---|---|---|
| Mass Ratio (%) | $SiO_2$ | 60.0 | 80.0 | 74.8 | 62.0 | 68.1 | 61.5 |
| | $Li_2O$ | 14.2 | 17.0 | 15.6 | 10.0 | 17.0 | 12.4 |
| | $K_2O$ | 7.8 | 0.5 | 2.7 | 8.3 | 4.4 | 7.0 |
| | $ZrO_2$ | 3.5 | 0.5 | 0.9 | 4.5 | 0.8 | 3.4 |
| | $P_2O_5$ | 4.4 | 2.0 | 2.5 | 5.5 | 4.0 | 4.6 |
| | ZnO | 3.2 | — | 1.1 | 4.0 | 1.8 | 2.5 |
| | SrO | 2.7 | — | 0.9 | 4.0 | 1.5 | 2.5 |
| | BaO | — | — | — | — | — | 2.7 |
| | $CeO_2$ | 4.2 | — | 1.5 | 1.7 | 2.4 | 3.4 |
| | Total | 100.0 | 100.0 | 100.0 | 100.0 | 100.0 | 100.0 |
| Test Result of Press Molding | Bending Strength (MPa) | 443 | 450 | 443 | 323 | 432 | 424 |
| | Solubility ($\mu g/cm^2$) | 27 | 25 | 27 | 50 | 32 | 28 |
| | Contrast Ratio | 0.32 | 0.25 | 0.26 | 0.47 | 0.40 | 0.38 |
| | Crystal System | LDS, LMS, LP | LDS, LP | LDS, LP | LDS, LMS, LP | LDS, LMS, LP | LDS, LMS, LP |
| | Seizure to Investment Material | Good | Good | Good | Good | Good | Good |
| Test Result of Machining | Bending Strength (MPa) | 432 | 440 | 435 | 320 | 432 | 444 |
| | Solubility ($\mu g/cm^2$) | 30 | 30 | 31 | 51 | 35 | 30 |
| | Contrast Ratio | 0.30 | 0.30 | 0.29 | 0.45 | 0.36 | 0.33 |
| | Crystal System | LDS, LMS, LP | LDS, LMS, LP | LDS, LP | LDS, LMS, LP | LDS, LMS, LP | LDS, LMS, LP |
| Test Result of Powder Molding | Bending Strength (MPa) | 388 | 355 | 389 | 310 | 376 | 386 |
| | Solubility ($\mu g/cm^2$) | 43 | 40 | 40 | 52 | 44 | 43 |
| | Contrast Ratio | 0.37 | 0.35 | 0.32 | 0.46 | 0.42 | 0.36 |
| | Crystal System | LDS, LMS, LP | LDS, LMS, LP | LDS, LP | LDS, LMS, LP | LDS, LMS, LP | LDS, LMS, LP |

TABLE 3

| | Component | Example 13 | Example 14 | Example 15 | Example 16 | Example 17 | Example 18 |
|---|---|---|---|---|---|---|---|
| Mass Ratio (%) | $SiO_2$ | 70.2 | 63.5 | 69.1 | 65.1 | 68.9 | 65.4 |
| | $Li_2O$ | 15.6 | 14.1 | 15.3 | 14.4 | 15.3 | 14.5 |
| | $K_2O$ | 0.5 | 10.0 | 2.2 | 8.0 | 6.0 | 5.7 |
| | $ZrO_2$ | 3.5 | 3.2 | 3.5 | 3.3 | 0.0 | 5.0 |
| | $P_2O_5$ | 4.2 | 3.8 | 4.1 | 3.8 | 4.1 | 3.9 |
| | ZnO | 1.9 | 1.7 | 1.8 | 1.8 | 1.8 | 1.7 |
| | SrO | 1.6 | 1.4 | 1.5 | 1.5 | 1.5 | 1.5 |
| | BaO | — | — | — | — | — | — |
| | $CeO_2$ | 2.5 | 2.3 | 2.5 | 2.4 | 2.4 | 2.3 |
| | Total | 100.0 | 100.0 | 100.0 | 100.0 | 100.0 | 100.0 |
| Test Result of Press Molding | Bending Strength (MPa) | 416 | 431 | 451 | 460 | 458 | 453 |
| | Solubility ($\mu g/cm^2$) | 40 | 29 | 20 | 24 | 27 | 28 |
| | Contrast Ratio | 0.30 | 0.35 | 0.28 | 0.21 | 0.36 | 0.27 |
| | Crystal System | LDS, LMS, LP | LDS, LMS, LP | LDS, LP | LDS, LP | LDS, LP | LDS, LP |
| | Seizure to Investment Material | Good | Good | Good | Good | Good | Good |

TABLE 3-continued

| | Component | Example 13 | Example 14 | Example 15 | Example 16 | Example 17 | Example 18 |
|---|---|---|---|---|---|---|---|
| Test Result of Machining | Bending Strength (MPa) | 420 | 432 | 443 | 430 | 445 | 440 |
| | Solubility (μg/cm²) | 30 | 35 | 30 | 30 | 30 | 36 |
| | Contrast Ratio | 0.32 | 0.36 | 0.33 | 0.34 | 0.37 | 0.32 |
| | Crystal System | LDS, LMS, LP | LDS, LMS, LP | LDS, LP | LDS, LMS, LP | LDS, LP | LDS, LMS, LP |
| Test Result of Powder Molding | Bending Strength (MPa) | 380 | 378 | 390 | 381 | 385 | 375 |
| | Solubility (μg/cm²) | 46 | 46 | 41 | 42 | 48 | 40 |
| | Contrast Ratio | 0.32 | 0.42 | 0.38 | 0.38 | 0.40 | 0.38 |
| | Crystal System | LDS, LMS, LP | LDS, LMS, LP | LDS, LMS, LP | LDS, LMS, LP | LDS, LMS, LP | LDS, LMS, LP |

TABLE 4

| | Component | Example 19 | Example 20 | Example 21 | Example 22 | Example 23 | Example 24 | Example 25 |
|---|---|---|---|---|---|---|---|---|
| Mass Ratio (%) | $SiO_2$ | 68.8 | 69.5 | 69.6 | 66.0 | 69.0 | 66.6 | 67.5 |
| | $Li_2O$ | 15.3 | 15.5 | 15.5 | 14.7 | 15.3 | 14.9 | 15.0 |
| | $K_2O$ | 6.0 | 4.5 | 4.5 | 4.3 | 4.5 | 4.4 | 4.4 |
| | $ZrO_2$ | 0.1 | 0.5 | 3.5 | 3.3 | 3.5 | 3.4 | 3.4 |
| | $P_2O_5$ | 4.1 | 4.1 | 1.0 | 6.0 | 2.0 | 5.0 | — |
| | $TiO_2$ | — | — | — | — | — | — | 4.0 |
| | ZnO | 1.8 | 1.9 | 1.9 | 1.8 | 1.8 | 1.8 | 1.9 |
| | SrO | 1.5 | 1.5 | 1.5 | 1.5 | 1.5 | 1.5 | 1.5 |
| | BaO | — | — | — | — | — | — | — |
| | $CeO_2$ | 2.4 | 2.5 | 2.5 | 2.4 | 2.4 | 2.4 | 2.3 |
| | Total | 100.0 | 100.0 | 100.0 | 100.0 | 100.0 | 100.0 | 100.0 |
| Test Result of Press Molding | Bending Strength (MPa) | 456 | 463 | 412 | 443 | 459 | 452 | 400 |
| | Solubility (μg/cm²) | 36 | 32 | 27 | 45 | 22 | 25 | 32 |
| | Contrast Ratio | 0.22 | 0.24 | 0.38 | 0.28 | 0.27 | 0.27 | 0.41 |
| | Crystal System | LDS, LP | LDS, LP | LDS, LP | LDS, LP | LDS, LP | LDS, LP | LDS, LP |
| | Seizure to Investment Material | Good | Good | Good | Good | Good | Good | Good |
| Test Result of Machining | Bending Strength (MPa) | 445 | 445 | 403 | 432 | 435 | 444 | 398 |
| | Solubility (μg/cm²) | 30 | 30 | 25 | 48 | 32 | 32 | 33 |
| | Contrast Ratio | 0.27 | 0.27 | 0.39 | 0.28 | 0.28 | 0.28 | 0.42 |
| | Crystal System | LDS, LMS, LP | LDS, LP | LDS, LMS, LP | LDS, LMS, LP | LDS, LMS, LP | LDS, LP | LDS, LMS, |
| Test Result of Powder Molding | Bending Strength (MPa) | 375 | 390 | 365 | 375 | 377 | 364 | 354 |
| | Solubility (μg/cm²) | 33 | 41 | 35 | 52 | 41 | 30 | 33 |
| | Contrast Ratio | 0.34 | 0.39 | 0.41 | 0.35 | 0.30 | 0.31 | 0.44 |
| | Crystal System | LDS, LMS, LP | LDS, LMS, LP | LDS, LMS, LP | LDS, LMS, LP | LDS, LMS, LP | LDS, LMS, LP | LDS, LMS, LP |

TABLE 5

| Component | | Example 26 | Example 27 | Example 28 | Example 29 | Example 30 | Example 31 |
|---|---|---|---|---|---|---|---|
| Mass Ratio (%) | $SiO_2$ | 64.3 | 69.5 | 65.0 | 62.2 | 69.0 | 68.8 |
| | $Li_2O$ | 14.3 | 15.5 | 14.5 | 13.8 | 15.3 | 15.3 |
| | $K_2O$ | 4.2 | 4.5 | 4.2 | 4.1 | 4.5 | 4.5 |
| | $ZrO_2$ | 3.2 | 3.5 | 3.2 | 3.1 | 3.5 | 3.5 |
| | $P_2O_5$ | 3.8 | 4.1 | 3.9 | 3.7 | 4.1 | 4.1 |
| | ZnO | — | — | — | 1.7 | 1.8 | 1.8 |
| | SrO | 8.0 | 0.5 | 7.0 | 1.4 | 1.5 | 1.5 |
| | BaO | — | — | — | — | — | — |
| | $CeO_2$ | 2.2 | 2.4 | 2.2 | 10.0 | — | 0.5 |
| | Total | 100.0 | 100.0 | 100.0 | 100.0 | 100.0 | 100.0 |
| Test Result of Press Molding | Bending Strength (MPa) | 423 | 470 | 465 | 445 | 465 | 455 |
| | Solubility ($\mu g/cm^2$) | 42 | 42 | 39 | 26 | 30 | 26 |
| | Contrast Ratio | 0.43 | 0.45 | 0.41 | 0.22 | 0.42 | 0.23 |
| | Crystal System | LDS, LP | LDS, LP | LDS, LMS, LP | LDS, LP | LDS, LP | LDS, LP |
| | Seizure to Investment Material | Good | Good | Good | Good | Good | Good |
| Test Result of Machining | Bending Strength (MPa) | 433 | 460 | 456 | 440 | 460 | 440 |
| | Solubility ($\mu g/cm^2$) | 40 | 44 | 40 | 32 | 40 | 30 |
| | Contrast Ratio | 0.40 | 0.41 | 0.39 | 0.27 | 0.42 | 0.25 |
| | Crystal System | LDS, LMS, LP | LDS, LMS, LP | LDS, LMS, LP | LDS, LMS, LP | LDS, LMS, LP | LDS, LP |
| Test Result of Powder Molding | Bending Strength (MPa) | 371 | 390 | 380 | 385 | 373 | 395 |
| | Solubility ($\mu g/cm^2$) | 43 | 43 | 41 | 47 | 49 | 41 |
| | Contrast Ratio | 0.40 | 0.40 | 0.45 | 0.30 | 0.45 | 0.31 |
| | Crystal System | LDS, LMS, LP | LDS, LMS, LP | LDS, LMS, LP | LDS, LMS, LP | LDS, LMS, LP | LDS, LMS, LP |

Comparative Examples

TABLE 6

| Component | | Comparative Example 1 | Comparative Example 2 | Comparative Example 3 | Comparative Example 4 | Comparative Example 5 |
|---|---|---|---|---|---|---|
| Mass Ratio (%) | $SiO_2$ | 66.6 | 66.9 | 66.9 | 81.2 | 59.4 |
| | $Al_2O_3$ | 2.5 | 2.5 | 2.5 | — | — |
| | $Li_2O$ | 15.2 | 15.2 | 15.2 | 12.3 | 14.4 |
| | $K_2O$ | 4.2 | 4.2 | 2.0 | 2.0 | 7.9 |
| | $ZrO_2$ | 0.7 | 0.7 | 0.7 | 1.0 | 3.6 |
| | $P_2O_5$ | 4.7 | 4.7 | 4.7 | 3.5 | 4.5 |
| | ZnO | 1.8 | 1.8 | 1.8 | — | 3.2 |
| | SrO | 1.6 | 1.6 | 3.8 | — | 2.7 |
| | BaO | — | — | — | — | — |
| | $CeO_2$ | 2.4 | 2.4 | 2.4 | — | 4.3 |
| | $La_2O_3$ | 0.3 | 0.0 | 0.0 | — | — |
| | Total | 100.0 | 100.0 | 100.0 | 100.0 | 100.0 |
| Test Result of Press Molding | Bending Strength (MPa) | 325 | 332 | 343 | 254 | 289 |
| | Solubility ($\mu g/cm^2$) | 128 | 119 | 120 | 56 | 64 |
| | Contrast Ratio | 0.83 | 0.81 | 0.77 | 0.73 | 0.71 |
| | Crystal System | LDS, LMS, LP | LDS, LMS, LP | LDS, LMS, LP | LDS, LMS, LP Cristobalite | LDS, LMS, LP |

TABLE 6-continued

|  | Component | Comparative Example 1 | Comparative Example 2 | Comparative Example 3 | Comparative Example 4 | Comparative Example 5 |
|---|---|---|---|---|---|---|
|  | Seizure to Investment Material | Poor | Poor | Poor | Good | Good |
| Test Result of Machining | Bending Strength (MPa) | 345 | 355 | 340 | 250 | 302 |
|  | Solubility ($\mu g/cm^2$) | 91 | 105 | 112 | 53 | 50 |
|  | Contrast Ratio | 0.73 | 0.79 | 0.79 | 0.72 | 0.72 |
|  | Crystal System | LDS, LMS, LP, AlPO4 | LDS, LMS, LP, AlPO4 | LDS, LMS, LP, AlPO4 | LDS, LMS, LP Cristobalite | LDS, LMS, LP |
| Test Result of Powder Molding | Bending Strength (MPa) | 284 | 277 | 268 | 220 | 289 |
|  | Solubility ($\mu g/cm^2$) | 145 | 140 | 138 | 58 | 54 |
|  | Contrast Ratio | 0.79 | 0.80 | 0.80 | 0.80 | 0.75 |
|  | Crystal System | LDS, LMS, LP | LDS, LMS, LP | LDS, LMS, LP | LDS, LMS, LP Cristobalite | LDS, LMS, LP |

TABLE 7

|  | Component | Comparative Example 6 | Comparative Example 7 | Comparative Example 8 | Comparative Example 9 | Comparative Example 10 |
|---|---|---|---|---|---|---|
| Mass Ratio (%) | $SiO_2$ | 71.8 | 65.3 | 70.4 | 63.2 | 66.0 |
|  | $Al_2O_3$ | — | — | — | — | — |
|  | $Li_2O$ | 9.5 | 17.7 | 15.6 | 14.1 | 14.7 |
|  | $K_2O$ | 4.3 | 4.3 | 0.3 | 10.3 | 4.3 |
|  | $ZrO_2$ | 4.7 | 3.3 | 3.5 | 3.2 | 5.5 |
|  | $P_2O_5$ | 3.6 | 3.9 | 4.2 | 3.8 | 3.9 |
|  | ZnO | 1.9 | 1.7 | 1.9 | 1.7 | 1.8 |
|  | SrO | 1.6 | 1.5 | 1.6 | 1.4 | 1.5 |
|  | BaO | 0.0 | 0.0 | 0.0 | 0.0 | 0.0 |
|  | $CeO_2$ | 2.6 | 2.3 | 2.5 | 2.3 | 2.3 |
|  | $La_2O_3$ | — | — | — | — | — |
|  | Total | 100.0 | 100.0 | 100.0 | 100.0 | 100.0 |
| Test Result of Press Molding | Bending Strength (MPa) | 267 | 365 | 375 | 375 | 355 |
|  | Solubility ($\mu g/cm^2$) | 53 | 75 | 56 | 96 | 45 |
|  | Contrast Ratio | 0.74 | 0.83 | 0.83 | 0.74 | 0.56 |
|  | Crystal System | LDS, LMS, LP Cristobalite | LDS, LMS, LP | LDS, LMS, LP | LDS, LMS, LP | LDS, LMS, LP |
|  | Seizure to Investment Material | Good | Poor | Poor | Poor | Poor |
| Test Result of Machining | Bending Strength (MPa) | 254 | 345 | 360 | 345 | 360 |
|  | Solubility ($\mu g/cm^2$) | 50 | 91 | 76 | 91 | 48 |
|  | Contrast Ratio | 0.72 | 0.73 | 0.74 | 0.73 | 0.55 |
|  | Crystal System | LDS, LMS, LP Cristobalite | LDS, LMS, LP | LDS, LMS, LP | LDS, LMS, LP | LDS, LMS, LP |
| Test Result of Powder Molding | Bending Strength (MPa) | 233 | 284 | 330 | 284 | 270 |
|  | Solubility ($\mu g/cm^2$) | 56 | 101 | 85 | 82 | 45 |

TABLE 7-continued

| Component | Comparative Example 6 | Comparative Example 7 | Comparative Example 8 | Comparative Example 9 | Comparative Example 10 |
|---|---|---|---|---|---|
| Contrast Ratio | 0.80 | 0.79 | 0.79 | 0.79 | 0.65 |
| Crystal System | LDS, LMS, LP Cristobalite | LDS, LMS, LP | LDS, LMS, LP | LDS, LMS, LP | LDS, LMS, LP |

TABLE 8

| | Component | Comparative Example 11 | Comparative Example 12 | Comparative Example 13 | Comparative Example 14 |
|---|---|---|---|---|---|
| Mass Ratio (%) | $SiO_2$ | 69.8 | 65.9 | 62.7 | 62.0 |
| | $Al_2O_3$ | 0.0 | 0.0 | 0.0 | 0.0 |
| | $Li_2O$ | 15.5 | 14.7 | 13.9 | 13.7 |
| | $K_2O$ | 4.5 | 4.3 | 4.1 | 4.0 |
| | $ZrO_2$ | 3.5 | 3.3 | 3.2 | 3.1 |
| | $P_2O_5$ | 0.8 | 6.2 | 3.7 | 3.7 |
| | ZnO | 1.9 | 1.8 | 1.7 | 1.6 |
| | SrO | 1.5 | 1.5 | 8.5 | 1.4 |
| | BaO | 0.0 | 0.0 | 0.0 | 0.0 |
| | $CeO_2$ | 2.5 | 2.3 | 2.2 | 10.5 |
| | $La_2O_3$ | 0.0 | 0.0 | 0.0 | 0.0 |
| | Total | 100.0 | 100.0 | 100.0 | 100.0 |
| Test Result by Press Molding | Bending Strength (MPa) | 325 | 376 | 345 | 359 |
| | Solubility ($\mu g/cm^2$) | 128 | 107 | 120 | 117 |
| | Contrast Ratio | 0.83 | 0.64 | 0.68 | 0.70 |
| | Crystal System | LDS, LMS, LP | LDS, LMS, LP | LDS, LMS, LP | LDS, LMS, LP |
| | Seizure to Investment Material | Poor | Poor | Poor | Poor |
| Test Result by Machining | Bending Strength (MPa) | 345 | 340 | 345 | 370 |
| | Solubility ($\mu g/cm^2$) | 91 | 92 | 78 | 65 |
| | Contrast Ratio | 0.73 | 0.73 | 0.73 | 0.73 |
| | Crystal System | LDS, LMS, LP | LDS, LMS, LP | LDS, LMS, LP | LDS, LMS, LP |
| Test Result by Powder Molding | Bending Strength (MPa) | 284 | 284 | 280 | 200 |
| | Solubility ($\mu g/cm^2$) | 114 | 130 | 98 | 92 |
| | Contrast Ratio | 0.79 | 0.79 | 0.79 | 0.79 |
| | Crystal System | LDS, LMS, LP | LDS, LMS, LP | LDS, LMS, LP | LDS, LMS, LP |

It was verified that in all Examples, the bending strengths were high, and high material strengths were developed. On the other hand, in Comparative Examples 1 to 7 and 9 to 14, the bending strengths were low, and sufficient material strengths were not developed.

As for the solubility, the solubility of all Examples were within the standard value (100 µg/cm²) of ISO6872, and a high chemical durability (low solubility) was exhibited in every Example. On the other hand, in Comparative Examples 1 to 3, 7 and 11 to 14, the solubility deviates from the standard value (100 µg/cm²) of ISO6872.

In each of Examples, the contrast ratio was 0.21 to 0.48 to exhibit a high transparency. On the other hand, in each of Comparative Examples, the contrast ratio was more than 0.65 to exhibit a low transparency in Press Molding, Machining and/or Powder Molding. Both in Examples and in Comparative Examples, with respect to the crystal system after the test, LDS was precipitated as the main crystals, and LMS and/or $Li_3PO_4$ were precipitated in trace amounts. Examples were free from the seizure to the investment material to give satisfactory results. On the other hand, in Comparative Examples 1 to 3 and 7 to 14, the seizure to the investment material was observed on the specimen surface in many cases.

From the above-described results, each of the dental lithium silicate glass ceramics obtained by heat treating the dental lithium silicate glass compositions of the present invention exhibited satisfactory results such as a high material strength, a high chemical durability and a high transparency in the same time. This is probably due to the fact that by heat treating the dental lithium silicate glass composition of the present invention, having specific content ranges of oxides and being free from $Al_2O_3$, the main crystals (lithium disilicate and/or lithium metasilicate) was precipitated efficiently and in a high density. Specifically, the development of the high strength and the improvement of the chemical stability are due to the $Al_2O_3$-free dental lithium silicate glass composition of the present invention; the improvement of the transparency is due to the improvement of the refractive index effected by the inclusion of $ZrO_2$ in the glassy portion surrounding the main crystals.

Consequently, the dental lithium silicate glass composition of the present invention drastically improves various properties as compared with conventional $Al_2O_3$-containing lithium silicate glass compositions.

INDUSTRIAL APPLICABILITY

The dental lithium silicate glass ceramic provided by the present invention has a high material strength, a high transparency and a high chemical stability (high chemical durability, low reactivity) allowing the ceramic concerned to be applied to a blank for press molding, a blank for machining and a powder porcelain, and is capable of being applied to various dental crown restorative materials in the restorative treatment of the dental field.

What is claimed is:

1. An $Al_2O_3$-free dental lithium silicate glass composition consisting of the following components:
   $SiO_2$: 60.0 to 80.0% by weight,
   $Li_2O$: 10.0 to 17.0% by weight,
   $K_2O$: 0.5 to 10.0% by weight,
   $ZrO_2$: 0.1 to 5.0% by weight,
   a nucleating agent: 1.0 to 6.0% by weight,
   a glass stabilizer: 0.0 to 8.0% by weight, and,
   a colorant: 0.0 to 10.0% by weight
   wherein the nucleating agent is one or more selected from the group consisting of $P_2O_5$, $TiO_2$, $WO_3$, $V_2O_5$, Pt and Ag, wherein the glass stabilizer is one or more selected from the group consisting of CaO, MgO, SrO, BaO, ZnO, $Y_2O_3$, $Ta_2O_5$, $Sb_2O_3$, $GeO_2$ and $B_2O_3$, and wherein the colorant is one or more selected from the group consisting of MnO, $Fe_2O_3$, $Tb_4O_7$, $Eu_2O_3$, $Ni_2O_3$, $Co_2O_3$, $Cr_2O_3$, $SnO_2$, $CeO_2$, $Nd_2O_3$, $Pr_6O_{11}$, $Sm_2O_3$, $V_2O_5$, $Dy_2O_3$, $Ho_2O_3$ and $Er_2O_3$.

2. The $Al_2O_3$-free dental lithium silicate glass composition according to claim 1, wherein,
the $Al_2O_3$-free dental lithium silicate glass composition consists of the following components:
$SiO_2$: 60.0 to 75.0% by weight,
$Li_2O$: 12.0 to 17.0% by weight,
$K_2O$: 2.0 to 8.0% by weight,
$ZrO_2$: 0.1 to 5.0% by weight,
the nucleating agent: 1.0 to 5.0% by weight,
the glass stabilizer: 0.5 to 7.0% by weight, and,
the colorant: 0.5 to 10.0% by weight.

3. The $Al_2O_3$-free dental lithium silicate glass composition according to claim 1, wherein,
the nucleating agent is $P_2O_5$.

4. The $Al_2O_3$-free dental lithium silicate glass composition according to claim 1, wherein,
the colorant is $CeO_2$.

5. A dental lithium silicate glass ceramic comprising a heat treated product of the glass composition according to claim 1, wherein a precipitate of a lithium metasilicate crystal and/or a lithium disilicate crystal is included.

6. A dental crown restorative material comprising a thermocompression molded article, a machined product and/or a built-up/fired product of the dental lithium silicate glass ceramic according to claim 5.

7. The $Al_2O_3$-free dental lithium silicate glass composition according to claim 2, wherein,
the nucleating agent is $P_2O_5$.

8. The $Al_2O_3$-free dental lithium silicate glass composition according to claim 2, wherein,
the colorant is $CeO_2$.

9. The $Al_2O_3$-free dental lithium silicate glass composition according to claim 3, wherein,
the colorant is $CeO_2$.

10. The $Al_2O_3$-free dental lithium silicate glass composition according to claim 7, wherein,
the colorant is $CeO_2$.

11. A dental lithium silicate glass ceramic comprising a heat treated product of the glass composition according to claim 2, wherein a precipitate of a lithium metasilicate crystal and/or a lithium disilicate crystal is included.

12. A dental crown restorative material comprising a thermocompression molded article, a machined product and/or a built-up/fired product of the dental lithium silicate glass ceramic according to claim 11.

13. A dental lithium silicate glass ceramic comprising a heat treated product of the glass composition according to claim 3, wherein a precipitate of a lithium metasilicate crystal and/or a lithium disilicate crystal is included.

14. A dental crown restorative material comprising a thermocompression molded article, a machined product and/or a built-up/fired product of the dental lithium silicate glass ceramic according to claim 13.

15. A dental lithium silicate glass ceramic comprising a heat treated product of the glass composition according to claim 4, wherein a precipitate of a lithium metasilicate crystal and/or a lithium disilicate crystal is included.

16. A dental crown restorative material comprising a thermocompression molded article, a machined product and/or a built-up/fired product of the dental lithium silicate glass ceramic according to claim 15.

17. The $Al_2O_3$-free dental lithium silicate glass composition according to claim 1, wherein,
the $Al_2O_3$-free dental lithium silicate glass composition consists of the following components:
$SiO_2$: 60.0 to 80.0% by weight,
$Li_2O$: 10.0 to 17.0% by weight,
$K_2O$: 0.5 to 10.0% by weight,
$ZrO_2$: 0.1 to 5.0% by weight,
the nucleating agent: 1.0 to 6.0% by weight,
the glass stabilizer: 0.0% by weight, and,
the colorant: 0.0 to 10.0% by weight.

* * * * *